United States Patent
Wang et al.

(10) Patent No.: US 12,233,610 B2
(45) Date of Patent: Feb. 25, 2025

(54) DEVICE AND METHOD FOR RADIALLY STRENGTHENING POLYLACTIC ACID TUBE

(71) Applicant: SHANGHAI BIO-HEART BIOLOGICAL TECHNOLOGY CO., LTD., Shanghai (CN)

(72) Inventors: Li Wang, Shanghai (CN); ChenZhao Zhang, Shanghai (CN); Tao Cai, Shanghai (CN); Junyi Wang, Shanghai (CN)

(73) Assignee: Shanghai Bio-Heart Biological Technology Co., Ltd., Shanghai (CN)

( * ) Notice: Subject to any disclaimer, the term of this patent is extended or adjusted under 35 U.S.C. 154(b) by 132 days.

(21) Appl. No.: 18/093,408

(22) Filed: Jan. 5, 2023

(65) Prior Publication Data
US 2023/0150213 A1      May 18, 2023

Related U.S. Application Data

(63) Continuation-in-part of application No. PCT/CN2021/083756, filed on Mar. 30, 2021.

(30) Foreign Application Priority Data

Jul. 14, 2020   (CN) .......................... 202010672032.1

(51) Int. Cl.
*B29C 71/00*       (2006.01)
*A61F 2/04*        (2013.01)
(Continued)

(52) U.S. Cl.
CPC .......... *B29C 71/0072* (2013.01); *B29C 71/02* (2013.01); *B29C 2071/027* (2013.01); *B29K 2067/046* (2013.01)

(58) Field of Classification Search
CPC ................ B29C 71/02; B29C 71/0072; B29C 2071/027; B29K 2067/046; A61F 2/04;
(Continued)

(56) References Cited

U.S. PATENT DOCUMENTS

| 2004/0050499 A1 | 3/2004 | Barody |
| 2008/0125707 A1 | 5/2008 | Wilson et al. |

(Continued)

FOREIGN PATENT DOCUMENTS

| CN | 1221675 A | 7/1999 |
| CN | 102126297 A | 7/2011 |

(Continued)

*Primary Examiner* — Galen H Hauth
*Assistant Examiner* — Baileigh Kate Darnell
(74) *Attorney, Agent, or Firm* — Carrier, Shende & Associates P.C.; Fulchand P. Shende; Joseph P. Carrier

(57) ABSTRACT

A device is provided for radially strengthening a polylactic acid tube, which includes a tubular mold, a rotating blade and a distal blade, wherein a rotating shaft of the rotating blade is arranged at an axial position of the tubular mold, a first end of the distal blade is movably connected to the rotating blade, and a second end of the distal blade is controlled by a control rod so as to open and close the distal blade. A strengthening method is provided, in which the device for radially strengthening a polylactic acid tube is used. The method includes loading a polylactic acid tube to be strengthened into the strengthening device, heating the strengthening device for a first preset time, rotating the rotating blade in a constant direction while opening the distal blade at a first speed such that the second end of the distal blade approaches the tubular mold, closing the distal blade and restoring the distal blade to an initial state after squeezing and scraping for a second preset time, cooling the strengthening device to room temperature, taking out a strengthened polylactic acid tube, and cutting off redundant sections. The tube strengthened by the above-mentioned (Continued)

strengthening device and method has a better wall thickness uniformity, more precise inner and outer diameter dimensions, with no axial orientation, and no thermal creep in a low temperature range such as body temperature, etc.

20 Claims, 3 Drawing Sheets

(51) Int. Cl.
  *A61F 2/82* (2013.01)
  *B29C 71/02* (2006.01)
  *B29K 67/00* (2006.01)

(58) Field of Classification Search
  CPC ...... A61F 2/82; A61F 2240/001; A61L 31/06; A61L 61/148; B29L 2023/00; B29L 2024/00; B29L 2031/7542
  See application file for complete search history.

(56) References Cited

U.S. PATENT DOCUMENTS

| | | | |
|---|---|---|---|
| 2015/0252825 A1* | 9/2015 | Lowth | F16B 2/06 24/493 |
| 2016/0022458 A1 | 1/2016 | Newell et al. | |
| 2016/0031150 A1 | 2/2016 | Gada et al. | |
| 2017/0203494 A1* | 7/2017 | Vyas | A61F 2/915 |

FOREIGN PATENT DOCUMENTS

| | | |
|---|---|---|
| CN | 104582643 A | 4/2015 |
| CN | 108016023 A | 5/2018 |
| CN | 109503916 A | 3/2019 |
| CN | 111559098 A | 8/2020 |
| WO | 02/055290 A1 | 7/2002 |

* cited by examiner

DEVICE AND METHOD FOR RADIALLY STRENGTHENING POLYLACTIC ACID TUBE

RELATED APPLICATIONS

This application is a continuation-in-part (CIP) application claiming benefit of PCT/CN2021/083756 filed on Mar. 30, 2021, which claims priority to Chinese Patent Application No. 202010672032.1 filed on Jul. 14, 2020, the disclosures of which are incorporated herein in their entirety by reference.

FIELD OF THE INVENTION

The present invention relates to the field of medical equipment, in particular to a device and method for radially strengthening a polylactic acid tube.

DESCRIPTION OF THE PRIOR ART

Biodegradable stents have become a potential alternative to traditional metal stents because they can degrade in the human body environment and be absorbed and metabolized by the human body. However, biological stents have the problem of a poor support force and toughness. In order to solve the problem, Chinese patent document CN 201711213237.8 discloses a method for preparing a polylactic acid and polylactic acid copolymer stent, the method involving putting an original tube into a tubular mold, heating the tube, injecting a high pressure gas into the original tube, such that the tube can be highly orientated in the radial direction, and further axially stretching the tube in the axial direction of the tube so as to achieve orientation of the tube in both the radial direction and the axial direction, whereby the strength and toughness of the material are significantly improved in the radial and axial directions. In addition, after annealing for a certain time, a complete crystalline system is formed, and the internal stress of the tube is released, which effectively improves the support force and toughness of the stent immediately and after storage and reduces a fracture phenomenon during the process of retraction and expansion of the stent.

However, this method is an inflation method, and the wall thickness of a tube formed by means of inflation cannot be accurately controlled. Since the diameter of the tube is expanded from a smaller diameter, the tube is prone to radial retraction and axial stretching under the influence of the body temperature after being implanted into the body, and the tube is prone to axial retraction under the influence of the body temperature after being implanted into the body.

Therefore, a person skilled in the art is being committed to developing a strengthening device and method for radially strengthening a polylactic acid tube without using an inflation method.

SUMMARY OF THE INVENTION

In view of the above-mentioned shortcomings of the prior art, the present invention aims to develop a novel non-inflation-type device and method for radially strengthening a polylactic acid tube, the device and method allowing the tube to have a better wall thickness uniformity, more precise inner and outer diameter dimensions, no axial orientation, thereby causing the polylactic acid tube to have no radial and axial retraction after strengthening is complete, and no thermal creep in a low temperature range (body temperature, etc.).

In order to achieve the above-mentioned object, the present invention provides a device for radially strengthening a polylactic acid tube, the device comprising a tubular mold, a rotating blade and a distal blade; a rotating shaft of the rotating blade is arranged at an axial position of the tubular mold and can rotate relative to the axial position; a first end of the distal blade is movably connected to an end of the rotating blade far away from the rotating shaft; and a second end of the distal blade is connected to a control rod, opening and closing are achieved under the control of the control rod, and a joint between the distal blade and the rotating blade is a swing center.

Furthermore, the tubular mold is a metal piece.

Furthermore, the second end of the distal blade is a rounded corner.

Furthermore, the rotating blade is made of an antirust material.

Furthermore, the antirust material is an antirust metal.

In a second aspect, the present invention further provides a method for radially strengthening a polylactic acid tube using the device for radially strengthening a polylactic acid tube, the method comprising the following steps:
1. loading the polylactic acid tube to be strengthened into the strengthening device, heating the strengthening device to a first temperature, and maintaining the first temperature for a first preset time;
2. rotating the rotating blade of the strengthening device in a constant direction while opening the distal blade of the strengthening device at a first speed, such that the second end of the distal blade approaches the metal mold of the strengthening device;
3. when the opening of the distal blade exceeds 2°, suspending the opening of the distal blade and heating the strengthening device to a second temperature T2; and after the second temperature is reached, continuing to open the distal blade until the distal blade is completely opened;
4. after squeezing and scraping for a second preset time, closing the distal blade at a second speed and restoring the distal blade to an initial state;
5. cooling the strengthening device to room temperature; and
6. taking out the strengthened polylactic acid tube, and cutting off redundant tube sections at both ends of the polylactic acid tube.

Furthermore, in step 1, the first temperature is a starting temperature T1 that is higher than the vitrification of the polylactic acid tube.

Furthermore, in step 3, the second temperature is an end temperature T2 of the vitrification of the polylactic acid tube.

Furthermore, in step 1, the first preset time is 5-30 min.

Furthermore, if the wall thickness of the polylactic acid tube is 50-500 μm, the first preset time is 5 min.

Furthermore, if the wall thickness of the polylactic acid tube is 150-200 μm, the first preset time is 20 min.

Furthermore, if the wall thickness of the polylactic acid tube is 300-500 μm, the first preset time is 30 min.

Furthermore, in step 2, the first speed is 0.1°/min. Furthermore, in step 4, the second speed is 0.1°/min. Furthermore, in step 2, the rotating speed of the rotating blade is 1-20 rpm. Furthermore, in step 3, the rotating speed of the rotating blade is 20-60 rpm.

Furthermore, in step 2, the constant direction is a direction in which the rotating blade rotates along the rotating shaft of the rotating blade to drive the distal blade to rotate along the swing center of the distal blade while facing away from the second end of the distal blade.

Furthermore, in step 4, the second preset time refers to the time taken for molecular chains of the polylactic acid tube to be oriented along the rotation direction of the rotating blade from a disordered arrangement to a circumferential orientation.

Furthermore, in step 6, the length of the tube sections cut off at both ends of the polylactic acid tube is 2 mm.

The present invention has the following technical effects:
1) The tube is confined by the external metal heating piece, and therefore, the outer diameter of the tube does not change; in addition, during the process of squeezing and scraping, the tube may have a slight overflow at both ends, resulting in a slight expansion of the inner diameter, and after the processing is completed, the overflow sections at both ends of the tube can be cut off to ensure the uniformity of the tube. Therefore, the strengthened tube has a better wall thickness uniformity, more precise inner and outer diameter dimensions, no diameter retraction after strengthening is complete, no axial orientation, thereby causing the polylactic acid tube to have no radial and axial retraction after strengthening is complete, and no thermal creep in a low temperature range (body temperature, etc.).
2) By controlling the rotating speed, the processing process is carried out at a lower rotating speed, and as the temperature increases, the rotating speed can be correspondingly increased, so as to realize accurate control of the temperature. If the rotating speed is too high, friction and heat may be induced during the processing process, which affects the control of the temperature of the tube and leads to a poor radial strengthening effect.

The concept, specific structure and produced technical effects of the present invention will be further illustrated below in conjunction with the drawings, in order to fully understand the objectives, features and effects of the present invention.

DETAILED DESCRIPTION OF THE PREFERRED EMBODIMENTS

Figure 1:
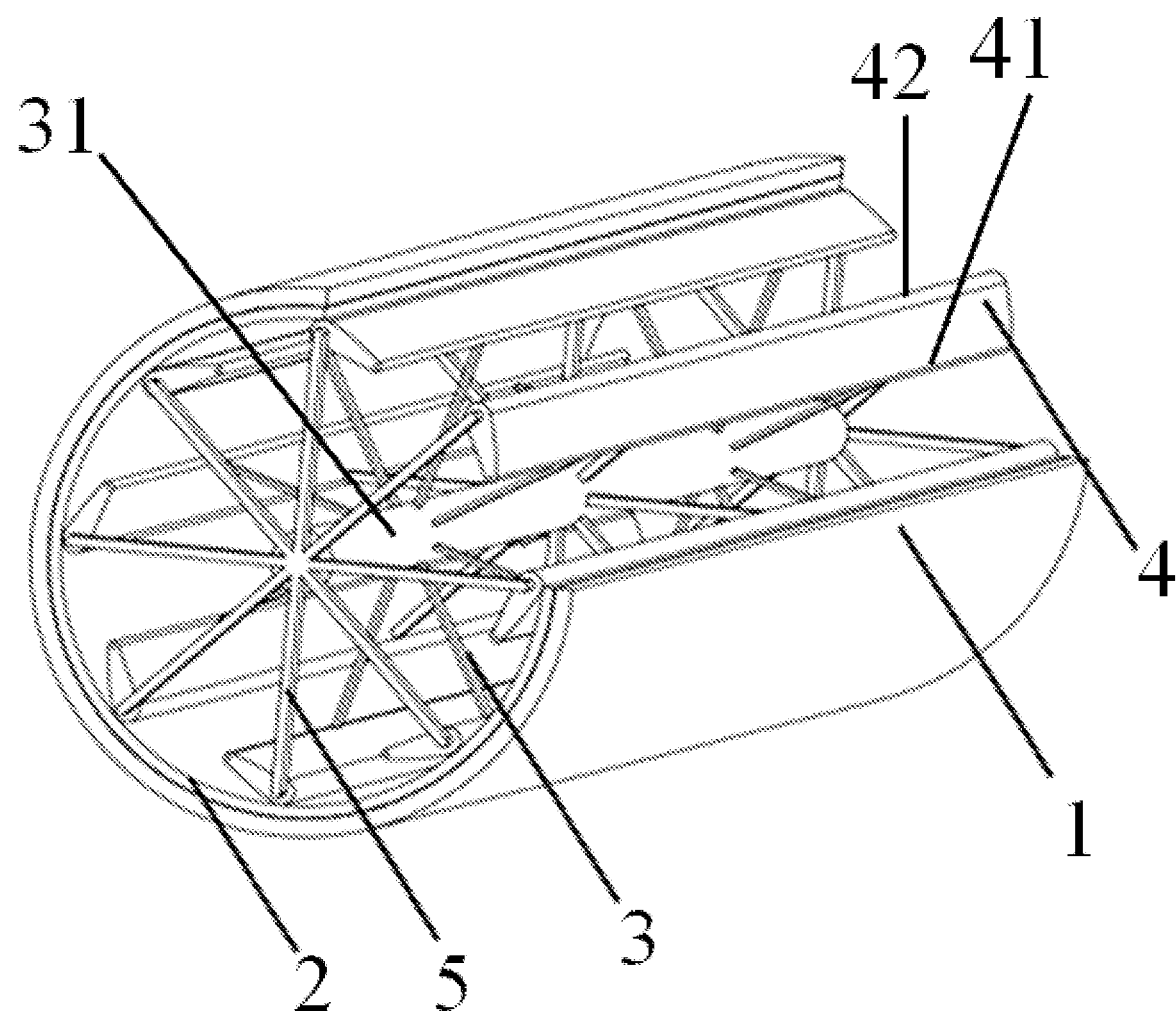
FIG. 1 is a schematic diagram of a strengthening device of a preferred embodiment of the present invention.

A plurality of preferred embodiments of the present invention are introduced below with reference to the description, in order to make the technical content thereof more clear and easier to understand. The present invention can be embodied in many different forms of embodiments, and the scope of protection of the present invention is not only limited to the embodiments mentioned herein.

In the drawings, structurally the same components are indicated by the same reference signs, and structurally or functionally similar constituent parts throughout are indicated by similar reference signs. The size and thickness of each constituent part as shown in the drawings are arbitrarily shown, and the present invention does not limit the size and thickness of each constituent part. In order to make the illustration clearer, the thickness of parts is appropriately exaggerated somewhere in the drawings.

Figure 2:
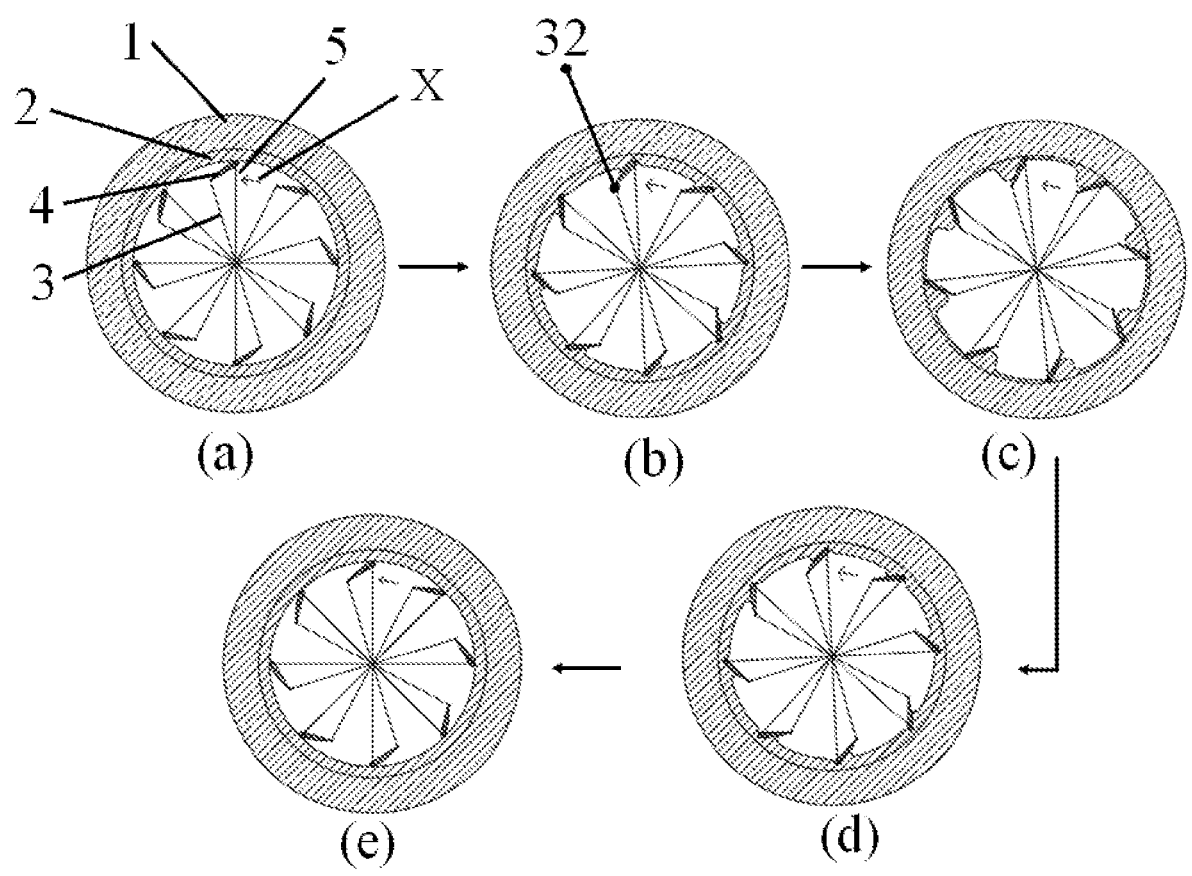
FIG. 2 is a cross-sectional schematic diagram of the working process of a strengthening device of a preferred embodiment of the present invention.

As shown in FIGS. 1 and 2, the device for radially strengthening a polylactic acid tube comprises a metal mold 1, a rotating blade 3, a distal blade 4 and a control rod 5, wherein the metal mold 1 is tubular, and an inner wall thereof is used for accommodating a polylactic acid tube 2 to be strengthened. The rotating blade 3, the distal blade 4 and the control rod 5 are all arranged inside the metal mold 1. A rotating shaft 31 of the rotating blade 3 is arranged at an axial position of the tubular metal mold 1, and the rotating blade 3 can rotate relative to the axial position of the metal mold 1. One end of the rotating blade 3 is connected to the rotating shaft 31, and the other end is movably connected to a first end 41 of the distal blade 4 so as to form a first movable joint 32; in addition, a second end 42 of the distal blade 4 opposite to the first end 41 is movably connected to the control rod 5. The control rod 5 can control the distal blade 4 to swing around the first movable joint 32 (i.e., taking the first movable joint 32 as a swing center), such that the included angle between the distal blade 4 and the metal mold 1 changes, wherein the direction in which the included angle increases is a direction in which the distal blade 4 opens. When the included angle between the distal blade 4 and the metal mold 1 reaches the maximum, the distal blade 4 is completely opened, wherein the value of the angle when the included angle between the distal blade 4 and the metal mold 1 reaches the maximum is determined according to actual requirements, and the specific numerical value thereof does not constitute a limitation to the present application. The direction in which the included angle decreases is a direction in which the distal blade 4 closes. The control rod 5 can control the distal blade 4 to swing, so as to control the opening and closing of the distal blade 4.

Figure 3:
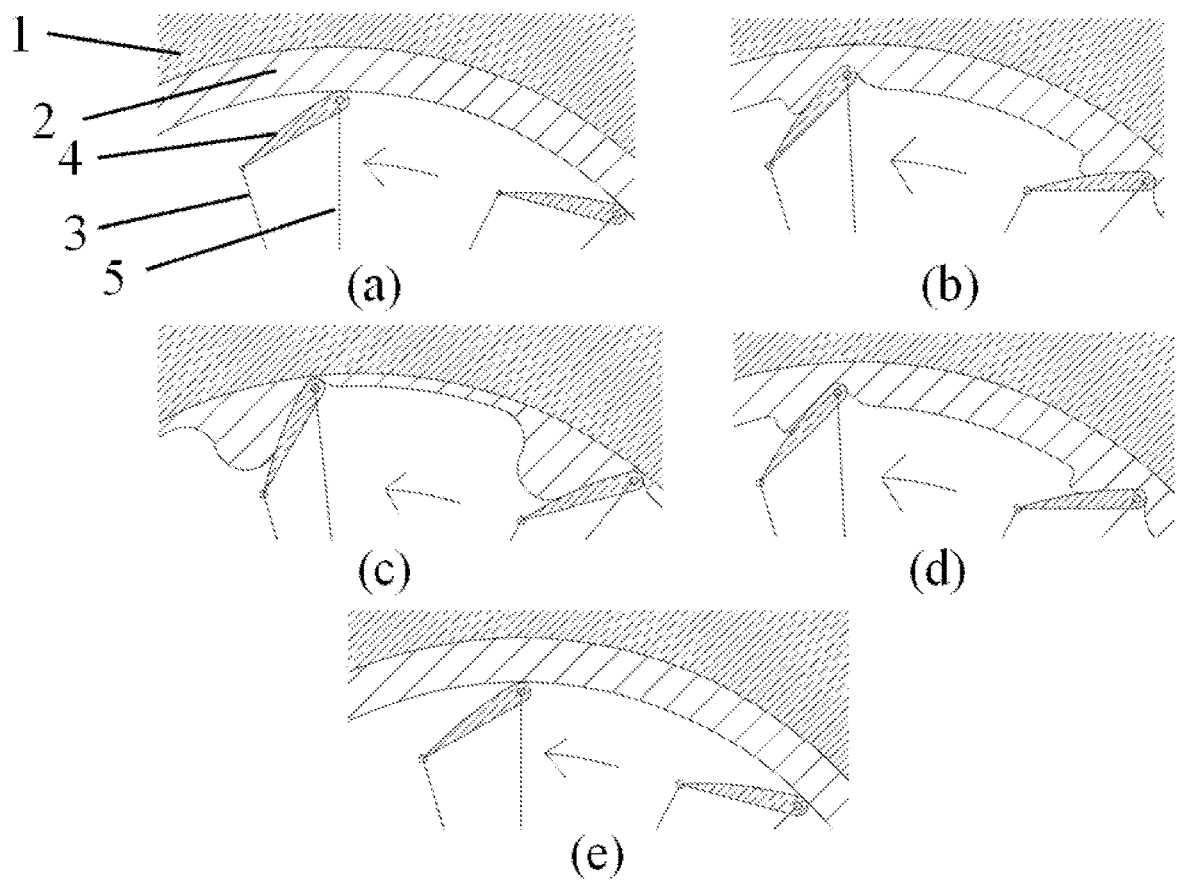
FIG. 3 is a partially enlarged cross-sectional schematic diagram of the working process of a strengthening device of a preferred embodiment of the present invention.

FIGS. 2 and 3 show the working process of the strengthening device, wherein (a) represents an initial state, (b) represents the opening process of the distal blade 4, (c) represents the state when the distal blade 4 is completely opened, (d) represents the closing process of the distal blade 4, and (e) represents a state in which the distal blade 4 is completely closed.

The second end 42 of the distal blade 4 may be set to have a rounded corner.

The metal mold 1 may be made of a metal with a good thermal conductivity. The rotating blade 3 may be made of an antirust material, preferably an antirust metal.

The method for radially strengthening a polylactic acid tube using the above-mentioned device for radially strengthening a polylactic acid tube is described below by means of several embodiments.

Embodiment 1

Figure 4:
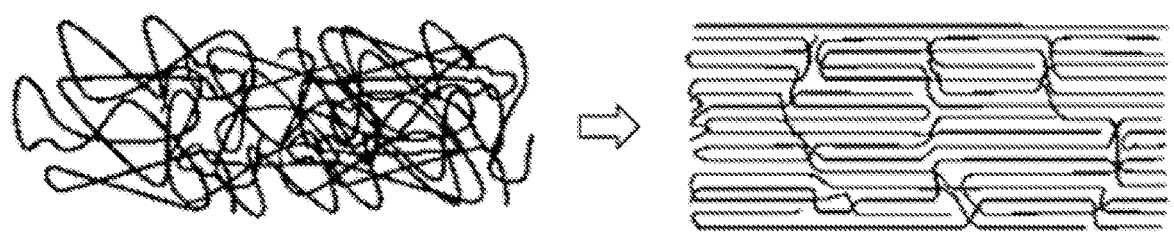
FIG. 4 is a schematic diagram of the change of the arrangement of molecular chains of a tube of a preferred embodiment of the present invention from disordered to ordered, wherein 1—metal mold, 2—polylactic acid tube, 3—rotating blade, 31—rotating shaft, 32—first movable joint, 4—distal blade, 41—first end of the distal blade, 42—second end of the distal blade, and 5—control rod.

As shown in FIGS. 1, 2 and 3, a polylactic acid tube 2 to be strengthened was put into a metal mold 1, wherein the wall thickness of the polylactic acid tube 2 was 50-100 μm, the metal mold 1 was heated to a starting temperature T1 that exceeded the vitrification of the polylactic acid tube, and the temperature was maintained for 5 min; the rotating blade 3 was then rotated along the rotating shaft 31 in a rotation direction as indicated by an X direction in FIGS. 2 and 3, so as to drive the distal blade 4 to rotate, wherein the X direction was a direction along the swing center of the distal blade 4 and away from the second end 42 of the distal blade 4, and the rotating speed of the rotating blade 3 was controlled between 1 and 20 rpm, and at the same time, the distal blade 4 was opened at a speed of 0.1°/min using the control rod 5 and gradually approached the metal mold 1; and when the opening of the distal blade 4 exceeded 2°, the opening of the distal blade 4 was suspended, and the temperature was raised to an end temperature T2 of the vitrification of the polylactic acid tube. After the end temperature T2 was reached, the rotating speed of the rotating blade 3 was controlled to 20-60 rpm, and the distal blade 4 continued to be opened until the distal blade 4 was completely opened; after squeezing and scraping for a period of time, the distal blade 4 was closed at a speed of 0.1°/min and restored to the initial state; and the metal mold 1 was cooled to room temperature, the strengthened polylactic acid tube 2 was took out, and redundant 2 mm tube sections at both ends of the processed tube were cut off. During the rotation process, the polylactic acid tube 2 was squeezed and scraped by the distal blade 4, and molecular chains thereof were oriented along the rotation direction of the blade, thereby achieving a change from a disordered arrangement to a circumferential orientation as shown in FIG. 4.

Embodiment 2

As shown in FIGS. 1, 2 and 3, a polylactic acid tube 2 to be strengthened was put into a metal mold 1, wherein the wall thickness of the polylactic acid tube 2 was 150-200 μm, the metal mold 1 was heated to a starting temperature T1 that exceeded the vitrification of the polylactic acid tube, and the temperature was maintained for 20 min; the rotating blade 3 was then rotated along the rotating shaft 31 in a rotation direction as indicated by an X direction in FIGS. 2 and 3, so as to drive the distal blade 4 to rotate, wherein the X direction was a direction along the swing center of the distal blade 4 and away from the second end 42 of the distal blade 4, and the rotating speed of the rotating blade 3 was controlled between 1 and 20 rpm, and at the same time, the distal blade 4 was opened at a speed of 0.1°/min using the control rod 5 and gradually approached the metal mold 1; and when the opening of the distal blade 4 exceeded 2°, the opening of the distal blade 4 was suspended, and the temperature was raised to an end temperature T2 of the vitrification of the polylactic acid tube. After the end temperature T2 was reached, the rotating speed of the rotating blade 3 was controlled to 20-60 rpm, and the distal blade 4 continued to be opened until the distal blade 4 was completely opened; after squeezing and scraping for a period of time, the distal blade 4 was closed at a speed of 0.1°/min and restored to the initial state; and the metal mold 1 was cooled to room temperature, the strengthened polylactic acid tube 2 was took out, and redundant 2 mm tube sections at both ends of the processed tube were cut off. During the rotation process, the polylactic acid tube 2 was squeezed and scraped by the distal blade 4, and molecular chains thereof were oriented along the rotation direction of the blade, thereby achieving a change from a disordered arrangement to a circumferential orientation as shown in FIG. 4.

Embodiment 3

As shown in FIGS. 1, 2 and 3, a polylactic acid tube 2 to be strengthened was put into a metal mold 1, wherein the wall thickness of the polylactic acid tube 2 was 300-500 μm, the metal mold 1 was heated to a starting temperature T1 that exceeded the vitrification of the polylactic acid tube, and the temperature was maintained for 30 min; the rotating blade 3 was then rotated along the rotating shaft 31 in a rotation direction as indicated by an X direction in FIGS. 2 and 3, so as to drive the distal blade 4 to rotate, wherein the X direction was a direction along the swing center of the distal blade 4 and away from the second end 42 of the distal blade 4, and the rotating speed of the rotating blade 3 was controlled between 1 and 20 rpm, and at the same time, the distal blade 4 was opened at a speed of 0.1°/min using the control rod 5 and gradually approached the metal mold 1; and when the opening of the distal blade 4 exceeded 2°, the opening of the distal blade 4 was suspended, and the temperature was raised to an end temperature T2 of the vitrification of the polylactic acid tube. After the end temperature T2 was reached, the rotating speed of the rotating blade 3 was controlled to 20-60 rpm, and the distal blade 4 continued to be opened until the distal blade 4 was completely opened; after squeezing and scraping for a period of time, the distal blade 4 was closed at a speed of 0.1°/min and restored to the initial state; and the metal mold 1 was cooled to room temperature, the strengthened polylactic acid tube 2 was took out, and redundant 2 mm tube sections at both ends of the processed tube were cut off. During the rotation process, the polylactic acid tube 2 was squeezed and scraped by the distal blade 4, and molecular chains thereof were oriented along the rotation direction of the blade, thereby achieving a change from a disordered arrangement to a circumferential orientation as shown in FIG. 4.

The preferred embodiments of the present invention have been described in detail above. It should be understood that many modifications and changes can be made by a person of ordinary skill in the art according to the concept of the present invention without involving any inventive effort. Therefore, any technical solutions that can be obtained by a person skilled in the art through logical analysis, reasoning or limited experiments on the basis of the prior art according to the concept of the present invention should be within the scope of protection as defined by the claims.

The invention claimed is:

1. A device for radially strengthening a polylactic acid tube, wherein the device comprises a tubular mold, a rotating blade and a distal blade; a rotating shaft of the rotating blade is arranged at an axial position of the tubular mold and can rotate relative to the axial position; one end of the rotating blade is connected to the rotating shaft, and the other end is movably connected to a first end of the distal blade; and a second end of the distal blade is connected to a control rod, opening and closing are achieved under the control of the control rod, and a joint between the distal blade and the rotating blade is a swing center.

2. The device for radially strengthening a polylactic acid tube of claim 1,
wherein the tubular mold is a metal piece.

3. The device for radially strengthening a polylactic acid tube of claim 1,
wherein the second end of the distal blade is a rounded corner.

4. The device for radially strengthening a polylactic acid tube of claim 1,
wherein the rotating blade is made of an antirust material.

5. The device for radially strengthening a polylactic acid tube of claim 4,
wherein the antirust material is an antirust metal.

6. The device for radially strengthening a polylactic acid tube of claim 1,
  wherein the wall thickness of the polylactic acid tube is 50-500 μm.

7. A method for radially strengthening a polylactic acid tube using the device for radially strengthening a polylactic acid tube of claim 1, wherein the method comprises the following steps:
  Step 1: loading the polylactic acid tube to be strengthened into the strengthening device, heating the strengthening device to a first temperature, and maintaining the first temperature for a first preset time;
  Step 2: rotating the rotating blade of the strengthening device in a constant direction while opening the distal blade of the strengthening device at a first speed, such that the second end of the distal blade approaches the metal mold of the strengthening device;
  Step 3: when the opening of the distal blade exceeds 2°, suspending the opening of the distal blade and heating the strengthening device to a second temperature T2; and
  after the second temperature is reached, continuing to open the distal blade until the distal blade is completely opened;
  Step 4: after squeezing and scraping for a second preset time, closing the distal blade at a second speed and restoring the distal blade to an initial state;
  Step 5: cooling the strengthening device to room temperature; and
  Step 6: taking out the strengthened polylactic acid tube, and cutting off redundant tube sections at both ends of the polylactic acid tube.

8. The method for radially strengthening a polylactic acid tube of claim 7, wherein in step 1, the first temperature is a starting temperature T1 that is higher than the vitrification of the polylactic acid tube.

9. The method for radially strengthening a polylactic acid tube of claim 7, wherein in step 3, the second temperature is an end temperature T2 of the vitrification of the polylactic acid tube.

10. The method for radially strengthening a polylactic acid tube of claim 7, wherein in step 1, the first preset time is 5-30 min.

11. The method for radially strengthening a polylactic acid tube of claim 10, wherein if the wall thickness of the polylactic acid tube is 50-500 μm, the first preset time is 5 min.

12. The method for radially strengthening a polylactic acid tube of claim 10, wherein if the wall thickness of the polylactic acid tube is 150-200 μm, the first preset time is 20 min.

13. The method for radially strengthening a polylactic acid tube of claim 10, wherein if the wall thickness of the polylactic acid tube is 300-500 μm, the first preset time is 30 min.

14. The method for radially strengthening a polylactic acid tube of claim 7, wherein in step 2, the first speed is 0.1°/min.

15. The method for radially strengthening a polylactic acid tube of claim 7, wherein in step 4, the second speed is 0.1°/min.

16. The method for radially strengthening a polylactic acid tube of claim 7, wherein in step 2, the rotating speed of the rotating blade is 1-20 rpm.

17. The method for radially strengthening a polylactic acid tube of claim 7, wherein in step 3, the rotating speed of the rotating blade is 20-60 rpm.

18. The method for radially strengthening a polylactic acid tube of claim 7, wherein in step 2, the constant direction is a direction in which the rotating blade rotates along the rotating shaft of the rotating blade to drive the distal blade to rotate along the swing center of the distal blade while facing away from the second end of the distal blade.

19. The method for radially strengthening a polylactic acid tube of claim 7, wherein in step 4, the second preset time refers to the time taken for molecular chains of the polylactic acid tube to be oriented along the rotation direction of the rotating blade from a disordered arrangement to a circumferential orientation.

20. The method for radially strengthening a polylactic acid tube of claim 7, wherein in step 6, the length of the tube sections cut off at both ends of the polylactic acid tube is 2 mm.

* * * * *